United States Patent [19]

Faghri

[11] Patent Number: 5,269,369
[45] Date of Patent: Dec. 14, 1993

[54] TEMPERATURE REGULATION SYSTEM FOR THE HUMAN BODY USING HEAT PIPES

[75] Inventor: Amir Faghri, Dayton, Ohio

[73] Assignee: Wright State University, Dayton, Ohio

[21] Appl. No.: 796,062

[22] Filed: Nov. 18, 1991

[51] Int. Cl.⁵ .................. A61F 7/00; F28D 15/02
[52] U.S. Cl. .................. 607/104; 165/104.4; 165/76; 165/46; 62/259.3; 607/108
[58] Field of Search ............ 165/46, 104.14, 76; 62/259.3; 128/402, 399

[56] References Cited

U.S. PATENT DOCUMENTS

| | | | |
|---|---|---|---|
| 3,000,616 | 9/1961 | Spangler | 165/46 |
| 3,289,748 | 12/1966 | Jennings | |
| 4,094,357 | 6/1978 | Sgroi | 165/46 |
| 4,706,672 | 11/1987 | Jones | 165/46 |
| 4,807,447 | 2/1989 | Macdonald et al. | |
| 4,884,304 | 12/1989 | Elkins | |
| 4,894,931 | 1/1990 | Senee et al. | |
| 4,962,761 | 10/1990 | Golden | |
| 4,966,145 | 10/1990 | Kikumoto et al. | |
| 4,966,226 | 10/1990 | Hamburgen | |
| 5,035,003 | 7/1991 | Rinehart | |
| 5,062,424 | 11/1991 | Hooker | |

OTHER PUBLICATIONS

"Heat Pipes for Hands", Amir Faghri, D. B. Reynolds, P. Faghri, *Mechanical Engineering*, Jun. 1989, pp. 70–74.

*Primary Examiner*—Albert W. Davis, Jr.
*Attorney, Agent, or Firm*—Killworth, Gottman, Hagan & Schaeff

[57] ABSTRACT

A temperature regulation system for the human body is provided which uses heat pipes to distribute energy to and from portions of a body to provide heating or cooling by redistributing body heat. The heat pipes are incorporated into a garment, a blanket and a pad which may be used for medical treatment or activities or for activities in environments having extreme temperatures. Supplemental means for heating and cooling are included to improve heating or cooling to a body, and to provide heating or cooling to limited areas of a body.

35 Claims, 10 Drawing Sheets

TEMPERATURE REGULATION SYSTEM FOR THE HUMAN BODY USING HEAT PIPES

BACKGROUND OF THE INVENTION

The present invention relates to temperature regulation of the human body, in particular, to the use of heat pipes in garments, blankets and pads to warm or cool the human body for activities in extreme temperature environments and for treatment of medical conditions.

The need to regulate body temperature exists where human activities are conducted in extreme temperature environments. Very cold environments are encountered by undersea divers, inhabitants of polar regions, pilots, mountain climbers and snow skiers, as well as by individuals who work in more pedestrian cold environments such as refrigerated containers. Very hot environments are encountered by those in diverse occupations such fire fighters, foundry workers and armored tank drivers.

The need for body temperature regulation also exists in the treatment of medical conditions. Individuals with impaired body temperature regulation systems, such as the elderly, stroke patients, and patients with spinal cord injuries or multiple sclerosis, may be subject to chronic hypothermia or hyperthermia. Victims of exposure, as well as patients having fever, dehydration, infection, and drug reactions may suffer temporarily from hypothermia or hyperthermia, and may require treatment including body temperature regulation.

Deliberate inducement of whole body hyperthermia has been found to be useful as a treatment for cancer, and has met with success. However, side effects range from fatigue to occasional mortality. Injury to temperature-sensitive body parts, such as the liver, has also been associated with whole body hypothermia. Because of these side effects, and the high labor costs associated with monitoring such treatment, regional, rather than whole body, hypothermia has found favor in the treatment of cancer. Inducement of regional or localized hyperthermia has, thus, also been used in the treatment of cancer, as well as in the treatment of joint diseases, such as capsulitis, tendinitis and lower back pain.

Various means have been developed to warm and cool the human body to achieve body temperature regulation needed for such activities and medical treatments. Cold suits, such as the garment shown by Jennings, U.S. Pat. No. 3,289,748, include circulating fluid systems powered by a pump or other means for circulating. See also, Macdonald et al, U.S. Pat. No. 4,807,447. In the garment of Jennings, serpentine tubes extend along the arms and legs of the wearer and converge at inlet and outlet manifolds. Cold suits, however, have the disadvantage of being heavy and are typically restrictive, causing exhaustion and cardiopulmonary distress in the wearer.

Hyperthermia blankets are also known wherein a single phase fluid loop winds back and forth through the blanket from inlet to outlet to cool the user. A chiller attached to the outlet of the fluid loop discharges heat from the hyperthermia blanket. Such blanket systems, however, have problems maintaining a constant blanket temperature throughout, and are heavy due to the weight of the circulating fluid. A blanket including heat pipes provides more uniform heating, as shown by Sgroi, U.S. Pat. No. 4,094,357. In the blanket of Sgroi, the heat pipes converge at one side of the blanket to be cooled by a refrigeration device or, alternatively, heated by a thermal energy source.

Suits and blankets having circulating fluid loops in similar configurations may also be used to provide heat to persons suffering from hypothermia. See, Macdonald et al and Sgroi. However, the same general disadvantages of weight, restriction of movement, and resulting exhaustion are present. Electric blankets are also well-known but often provide uneven heating, and subject the user to low-level electromagnetic radiation. Nonetheless, whether used for heating or cooling, such suits and blankets generally disadvantageously require external connections and/or require external power sources.

Numerous devices have been developed for regional, therapeutic heat transfer. Jones, U.S. Pat. No. 4,706,672 discloses a passive thermal transfer device in which metal fibers woven into a mesh act as a heat sink to draw heat from an afflicted area for dissipation. Golden, U.S. Pat. No. 4,962,761 discloses a thermal bandage to heat or cool an area of the skin, wherein a circulating fluid is used to carry heat to or from the afflicted part. However, the need continues to exists for improved means for applying heat to specific areas of the human body for the treatment of disease which will avoid damage to adjacent tissues and structures.

SUMMARY OF THE INVENTION

The present invention meets the need for lightweight, comfortable suits and blankets for body temperature regulation by using heat pipes to redistribute body heat and to provide supplemental heat from external sources. A temperature regulation system for the human body results, taking the form of garments, blankets and pads. In at least one embodiment of both the garment and blanket, the need for connection to an external source of fluid or power is eliminated. The present invention further provides for an improved pad incorporating heat pipes for use in regional, therapeutic heat transfer.

Garments

In a first embodiment, the garment of the present invention is made of a supporting fabric, such as a net fabric, which is shaped to cover at least a portion of a human body including a portion of the torso. The garment may thus be in the shape of a whole body suit, vest, jacket, pants, shorts, or other clothing articles. A plurality of flexible heat pipes are provided which are supported by the garment fabric. In accordance with the first embodiment, the heat pipes are positioned to provide heat transfer between one or more separate portions of the body. A garment for use in cold environments, such as a body suit, pants or jacket, may, thus, include heat pipes which extend from the torso of the body, which is typically warmer, to an extremity. The torso is thereby used as a heat source to warm any extremity such as the head, arms, hands, legs and feet, or portions thereof. As well, warmer, more central portions of the torso may be used in a garment, such as a vest, to distribute heat to other parts of the torso. A garment for use in warm environments, such as shorts, vests or hooded articles, may include heat pipes which extend from the head or other heat-sensitive areas, to cooler portions of the body, or to the outer surface of the garment to remove heat from the head or other heat-sensitive areas. The first embodiment, thus, permits body temperature to be regulated to a more uniform level by redistributing heat, as needed, to provide warming or cooling from one body area to another to enable an individual to carry out activities, or to assist a patient in satisfying medical needs for heating or cooling.

In a second embodiment, the garment of the first embodiment further includes a heat exchanger, a portion of which intersects one or more of the heat pipes to provide heat transfer between one or more portions of the body and the heat exchanger. The heat exchanger includes a heat exchanger element which is preferably disposed in the torso area of the garment, a circulating fluid loop, and a means for heating or means for cooling. Where the garment is to be used in cold environments, the heat exchanger includes means for heating the circulating fluid, and where used in hot environments, includes means for cooling the circulating fluid. Alternatively, the heat exchanger may include a heat exchanger element including electrical resistive heaters, preferably disposed in the torso area, and an external source of electrical power. The heat exchanger, further, preferably includes a temperature control device, such as a thermocouple or thermostat. Temperature control is of particular interest where the present invention is used for deliberate inducement of hyperthermia for medical treatment, or to provide controlled heating or cooling for hypothermia or hyperthermia patients.

A third embodiment of the garment of the present invention is a hybrid of the first and second embodiments thereof. The third embodiment includes a heat exchanger of the second embodiment to supply supplemental heating or cooling from the heat exchanger to at least one portion of a body, while one or more heat pipes provide heat transfer between portions of a body in accordance with the first embodiment.

In a fourth embodiment, the garment of the present invention includes at least two heat exchangers which intersect separate groups of one or more heat pipes to provide heat transfer between separate portions of a body and the heat exchangers, permitting selective and simultaneous heating or cooling of separate portions of the body. For example, in a garment such as a body suit, this fourth embodiment provides a means to overcome problems with damage to heat-sensitive organs when whole body hyperthermia is induced for medical treatment. Heat may be applied to major portions of the body to induce hyperthermia with one heat exchanger having means for heating, while portions of the body having heat-sensitive organs may be cooled with another heat exchanger having means for cooling.

In accordance with the present invention, the heat pipes are preferably connected to the fabric by adjustable and removable means for connecting, such as velcro connectors. That is, such means for connecting may be made fastenable at intervals to the fabric of the garment, to permit variable positioning of the heat pipes, as desired to suit the individual. Thus, for example, if the garment is to be worn by a wheelchair or bed patient, the heat pipes can be routed or re-routed for comfort. The heat pipes may be attached to the inside of the garment, so that no fabric is between the body and the heat pipe, to enhance transfer of heat from the body, or may be attached so that at least one layer of fabric separates the heat pipe from the wearer. Further, a plurality of fabric layers may be provided, with the heat pipes enclosed between two layers. Access to provide variable positioning of the heat pipes may be assured by use of closure devices, such as zippers, to connect and permit separation of fabric layers of the garment.

Blankets

In accordance with the present invention, a blanket is provided which regulates body temperature by using heat pipes to redistribute body heat and to provide supplemental heat from external sources.

In a first embodiment, the blanket of the present invention is made of a supporting fabric layer which is sufficiently large to cover at least the torso portion of a human body. A plurality of flexible heat pipes are provided which are supported by the garment fabric, and connected by means for connecting, such as are described above for the garment. In accordance with the first embodiment, the heat pipes are positioned to provide heat transfer between two or more areas of the blanket and adjacent portions of the body. Thus, the blanket encourages the body temperature to be regulated to a more uniform level by redistributing heat as needed to provide warming or cooling. When used to warm individuals subject to hypothermia, the heat pipes which extend from the torso of the body, which is typically warmer, towards other parts of the torso or an extremity, such as the feet or head. The torso is thereby used as a heat source. When used to cool individuals subject to hyperthermia, the heat pipes extend outward from the torso, head or heat-sensitive portions of the body, to cooler areas at the periphery of the blanket, or to an outer surface of the blanket to discharge heat by radiation or ambient air circulation. The first embodiment, thus, permits body temperature to be regulated to a more uniform level, or reduced, by redistributing heat needed to provide warming or cooling for an individual. The first embodiment is useful in satisfying medical needs as well as providing increased comfort for individuals who sweat or develop cold feet during rest or sleep.

In a second embodiment, the blanket of the first embodiment further includes one or more heat exchangers, portions of which intersect one or more of the heat pipes. The heat exchanger(s) provide heating or cooling to at least one area of the blanket and adjacent portions of a body while, simultaneously, one or more heat pipes provide heat transfer between areas of the blanket and adjacent portions of a body in accordance with the structure disclosed in the first embodiment. As previously discussed with regard to the garment, the heat exchangers include a heat exchanger element, preferably generally centrally disposed in the blanket, a circulating fluid loop, and means for heating or means for cooling. Where the heat exchanger is to be used for heating an area of the blanket and adjacent portions of the user, the heat exchanger includes means for heating the circulating fluid, and where used to cool, includes means for cooling the circulating fluid. Alternatively, the heat exchanger may include a heat exchanger element including electrical resistance heaters, preferably disposed in the torso area, and an external source of electrical power. Inclusion of a temperature control device is also preferred for reasons discussed above. The second embodiment makes possible the use of the blanket for inducing heating or cooling in one area and adjacent portions of a body, while thermal energy is redistributed to or from other areas and portions.

A third embodiment of the blanket of the present invention includes two heat exchangers, as described in the second blanket embodiment, to provide heating and/or cooling from the heat exchangers to separate portions of a blanket and adjacent portions of a body.

Thus, the blanket may be used in the inducement of hyperthermia for medical treatment, while providing cooling to heat-sensitive organs.

Pads

Finally, the pad of the present invention is made of a supporting fabric layer, which is sufficiently large to cover only a small portion of a body, and one or more flexible heat pipes. The pad further includes a heat exchanger which intersects the heat pipes, but may be located entirely remote from the pad or disposed, at least in part, thereon. The heat pipes are supported by the fabric and positioned to provide regional or local heat transfer between the heat exchanger and the pad. The pad provides regional or local control and regulation of body temperature as needed to provide warming or cooling, primarily for medical applications. However, the pad may also be used to warm portions of individuals who are subject to hypothermia, or to cool portions of individuals subject to hyperthermia. The heat exchanger used in the pad of the present invention may be of the fluid or electrical types discussed above with regard to garments and blankets.

Heat pipes provide very high thermal conduction, typically an order of magnitude higher than conventional conductors. A working fluid circulates therein, alternately vaporizing at the evaporation end to absorb thermal energy, and condensing at the condenser end to release thermal energy. Condensed working fluid returns to the evaporation end by capillary flow along a wick structure. The working fluid used depends on the particular application. By way of example and not limitation, in the present invention, the heat pipe may include methanol, acetone, ethanol or water as a working fluid. The wick structure may be made of various materials, the choice of which depends on the application and working fluid used. By way of example and not limitation, wick materials which may be used in the present invention include fiber mesh, screens, porous plastic wicks, and sintered powder metal and plastic wicks. In accordance with the present invention, the preferred wick is comprised of carbon fibers to promote high capillary pressures and promote return flow.

Accordingly, it is an object of the present invention to provide a garment in which heat pipes provide or receive heat at various parts of the body to regulate body temperature without need for external connections to fluid or power sources.

It is a further object of the present invention to provide a blanket having heat pipes which provide even temperatures throughout without use of external fluids or power sources.

It is a further object of the present invention to provide a pad having heat pipes which provide or receive heat for regional control of body temperature.

It is a still further object of the present invention to provide a garment, blanket or pad having heat pipes, and including auxiliary heating or cooling to all or part of an body.

It is a further object of the present invention to provide a garment or blanket having heat pipes which simultaneously provide both heating and cooling of separate body areas.

DETAILED DESCRIPTION OF THE PREFERRED EMBODIMENT

Garments

Figure 1:
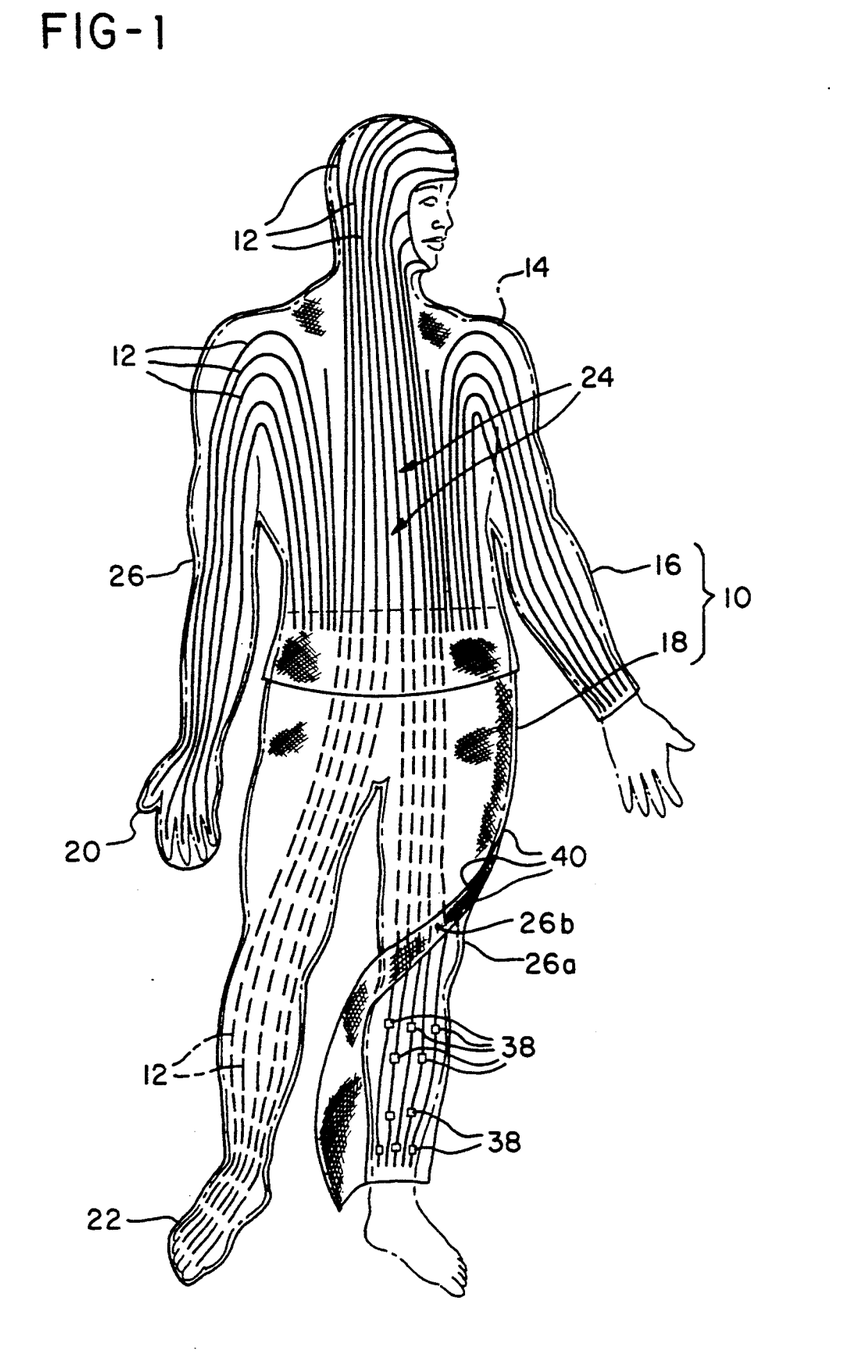
FIG. 1 is a schematic diagram of the garment of the present invention in accordance with the first embodiment in a two-piece configuration.

Referring to FIG. 1 a lightweight, comfortable garment 10 for body temperature regulation is shown which uses heat pipes 12 to redistribute body heat from the torso area 24 of a body 14 to the extremities, such as the head, arms, hands, legs and feet. No connection to external power or fluid sources is required. This first embodiment is representatively shown as a two-piece garment, consisting of a pull-over 16 and pants 18, and its configuration with and without hand and foot enclosures 20, 22, respectively, is illustrated.

In a first embodiment, shown in FIG. 1, the garment 10 of the present invention is made of a supporting fabric 26, such as a net fabric, which is shaped to cover at least a portion of a human body 14 including a portion of the torso 24. The garment 10 may, thus, be in the shape of a whole body suit (FIG. 2B), vest or shorts (FIG. 2A), jacket or pants (FIG. 1), or other clothing articles. A plurality of flexible heat pipes 12 are provided, which are supported by the garment fabric 26. While heat pipes 12 are shown on the front of the body 14, substantially corresponding heat pipes 12 may be positioned along the back side of body 14 in addition to or instead of the heat pipes 12 on the front of body 14.

Figure 9:
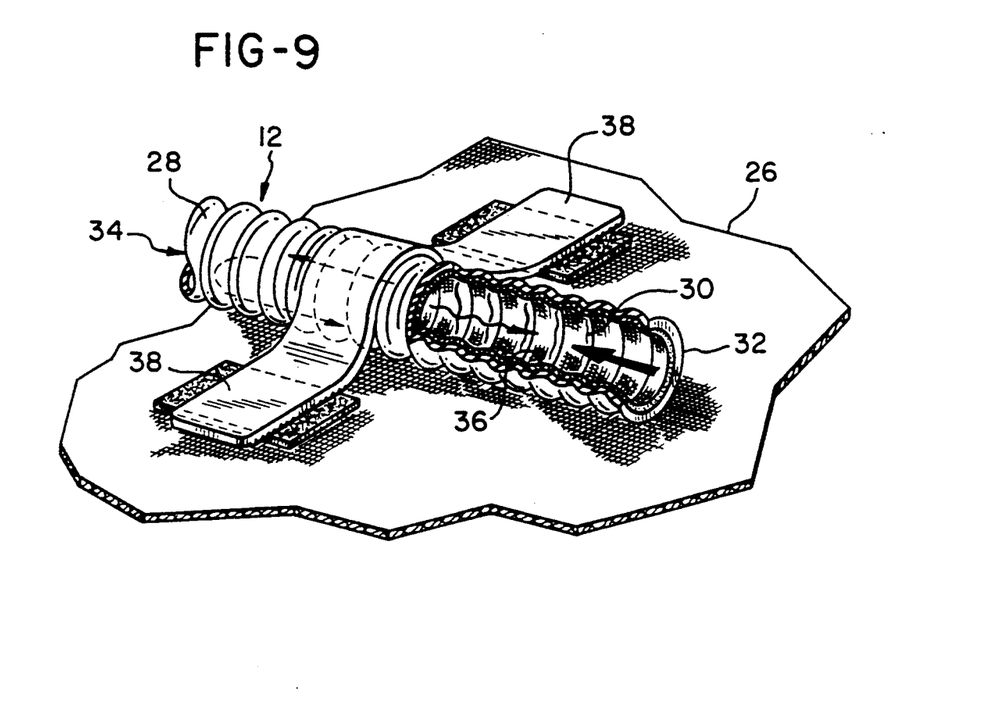
FIG. 9 is a schematic perspective view of a representative heat pipe and the means for attaching heat pipes of the present invention.
Figure 10:
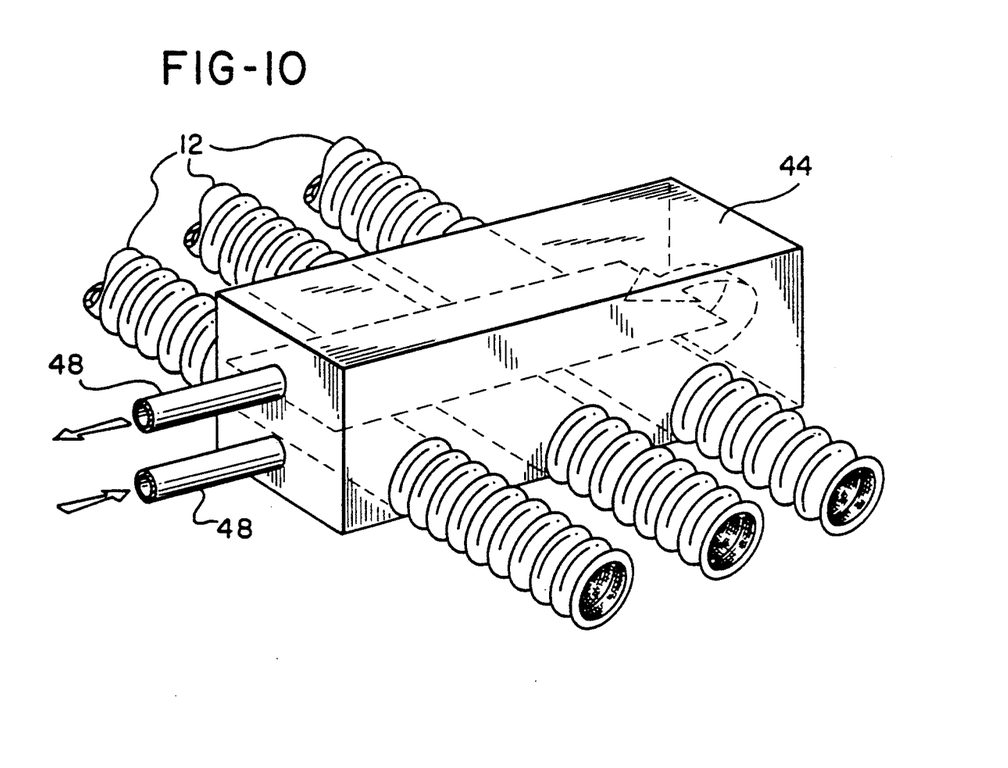
FIG. 10 is a schematic representative view of a heat exchanger of the present invention.

Heat pipes 12 used in the garments 10, blankets 70 and pads 80 of the present invention, are representatively shown in FIGS. 9 and 10. Heat pipes 12 have very high thermal conductivity, generally an order of magnitude greater than direct conduction by metallic conductors. Heat pipes 12 typically include a working fluid 30 which evaporates at one end to absorb thermal energy, and condenses at the other releasing thermal energy. Typically, the evaporation end 32 and condensation end 34 are separated by an adiabatic section, also referred to as a transport section. Working fluid 30 formed at the condensing end typically flows back to the evaporation end by capillary flow along a wick structure of wick 36. Heat pipes 12 can transfer heat at any point along the heat pipe. Evaporator, adiabatic, and condenser sections may be established simply by positioning heat sinks for condenser sections, and heat sources for evaporator sections along the heat pipe 12. In some cases, the adiabatic section may be eliminated completely.

In accordance with the present invention, the heat pipe 12 preferably comprises a small diameter, flexible tube 28, such as a corrugated stainless steel tube. Alternatively, tube 28 may be comprised of a polymer, such as polychlorotrifluoroethylene (PCTFE) available under the trademark KEL-F from 3M Corporation. Additionally, such polymers may also be coated with a thin film of metal, such as copper, to significantly reduce moisture permeation. There are many choices for the wick material as well as the working fluid, depending on the application and depending on the compatibility of the wick, working fluid and tube material. By way of example and not limitation, the working fluid 30 in heat pipe 12 may be methanol, acetone, ethanol or water. Further, heat pipe 12 preferably includes a wick 36 of carbon fibers which provide high capillary pressures and promote return flow. Flexible heat pipes with $\frac{3}{8}$ inch diameter corrugated stainless steel tubing with carbon filter wicks are available commercially from Fujikura LTD, Tokyo, Japan.

Figure 2A:
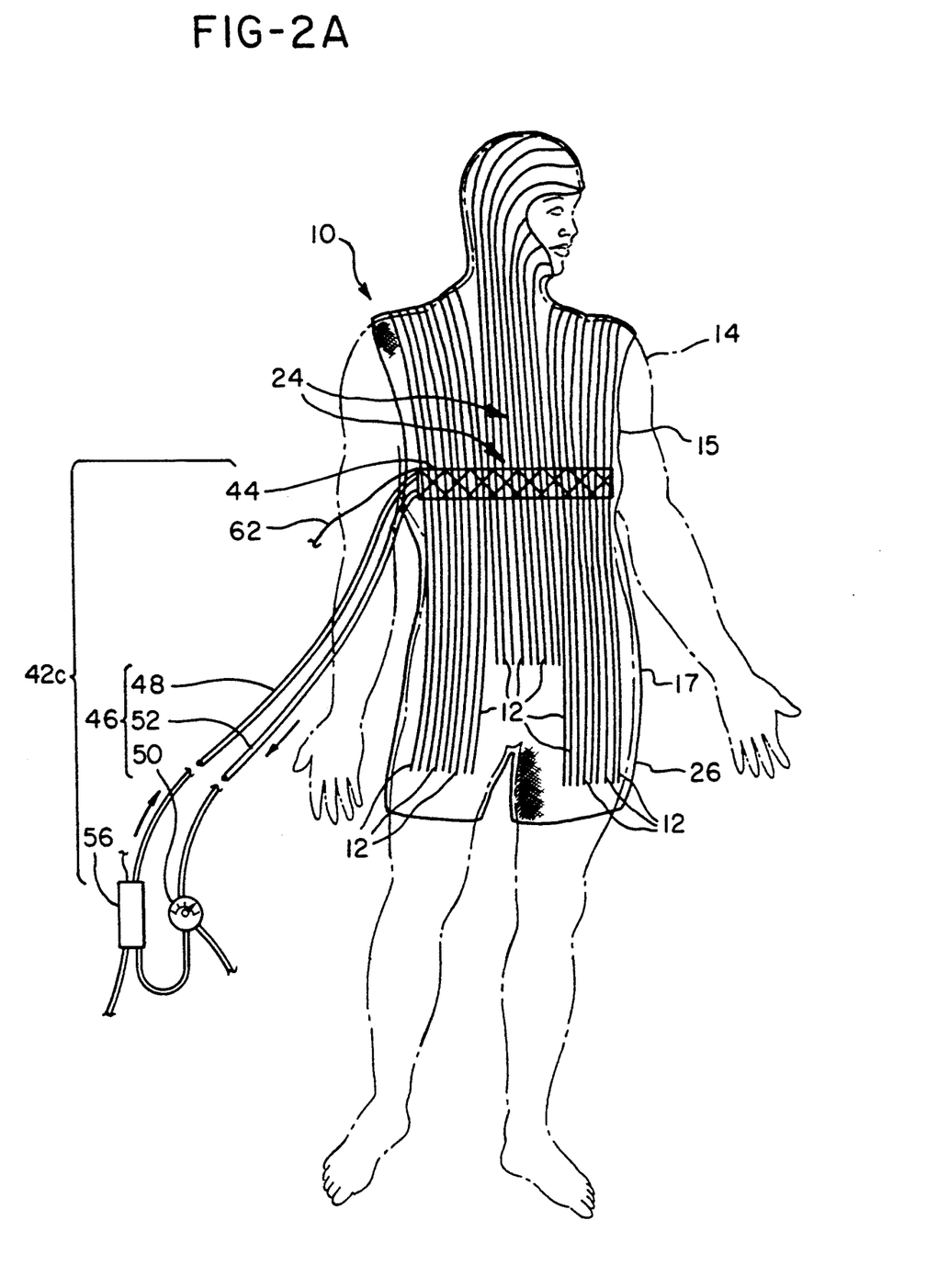
FIGS. 2A and 2B are schematic diagrams of the garment of the present invention in accordance with the second embodiment including means for cooling and means for heating, respectively, both in a body suit configuration.

As shown in FIG. 1, and applicable to the garment 10, blanket 70 and pad 80 of the present invention, the heat pipes 12 are preferably connected to the fabric 26 by means for connecting 38, such as velcro connectors. Such means for connecting 38 may be made fastenable at intervals to the fabric 26 of the garment 10, to permit variable positioning of the heat pipes 12, as desired to suit the individual body and needs. Thus, for example, if the garment 10 is to be worn by a wheelchair patient or bed patient, the heat pipes 12 can be routed for comfort, and positioned to prevent the patient from sitting or lying directly thereon. The heat pipes 12 may be attached to the inside of the garment 10, as shown in FIG. 2A, to promote heat transfer by direct contact with the body 14, or may be attached so that at least one layer of fabric separates the heat pipe 12 from the body, as shown in FIG. 1. Further, a plurality of fabric layers 26a, 26b may be provided, with the heat pipes 12 enclosed between two layers. Access to provide variable positioning of the heat pipes 12 may be assured by use of closure devices 40, such as zippers, on the garment 10.

In accordance with the first embodiment, the heat pipes 12 are positioned to provide heat transfer between one or more separate portions of the body 14. A garment 10 for use in cold environments, such as a body suit 19, pants 18 or jacket 16, may, thus, include heat pipes 12 which extend generally from the torso 24 of the body 14, which is typically warmer, to an extremity, such as an arm, leg, hand foot or the head. The torso 24 is thereby used as a heat source. As well, warmer, more central portions of the torso 24 may be used in a garment 10, as shown in FIG. 1, to distribute heat to other parts of the torso 24. A garment 10 for use in warm environments may be configured as shorts 17, vests 15 or hooded articles. Such garments 10 include heat pipes 12 which extend from the head or other heat-sensitive areas, to cooler portions of the body 14, such as the thigh or legs, or to an outer surface of the garment 10 to remove heat from the head or other heat-sensitive areas and dissipate it at cooler parts of the body 14. For example, the heat pipes 12 extending to the hood of jacket 16 in FIG. 1 may be used to remove heat from the head to the thighs, if the evaporation ends 32 of the heat pipes 12 are placed near the head and the condensation end 34 is placed near the thigh and hip areas. The first embodiment, thus, permits body temperature to be regulated to a more uniform level by redistributing heat as needed to provide warming or cooling, as needed for an individual to carry out activities or as required to assist a patient in satisfying medical needs for heating or cooling.

Figure 2B:
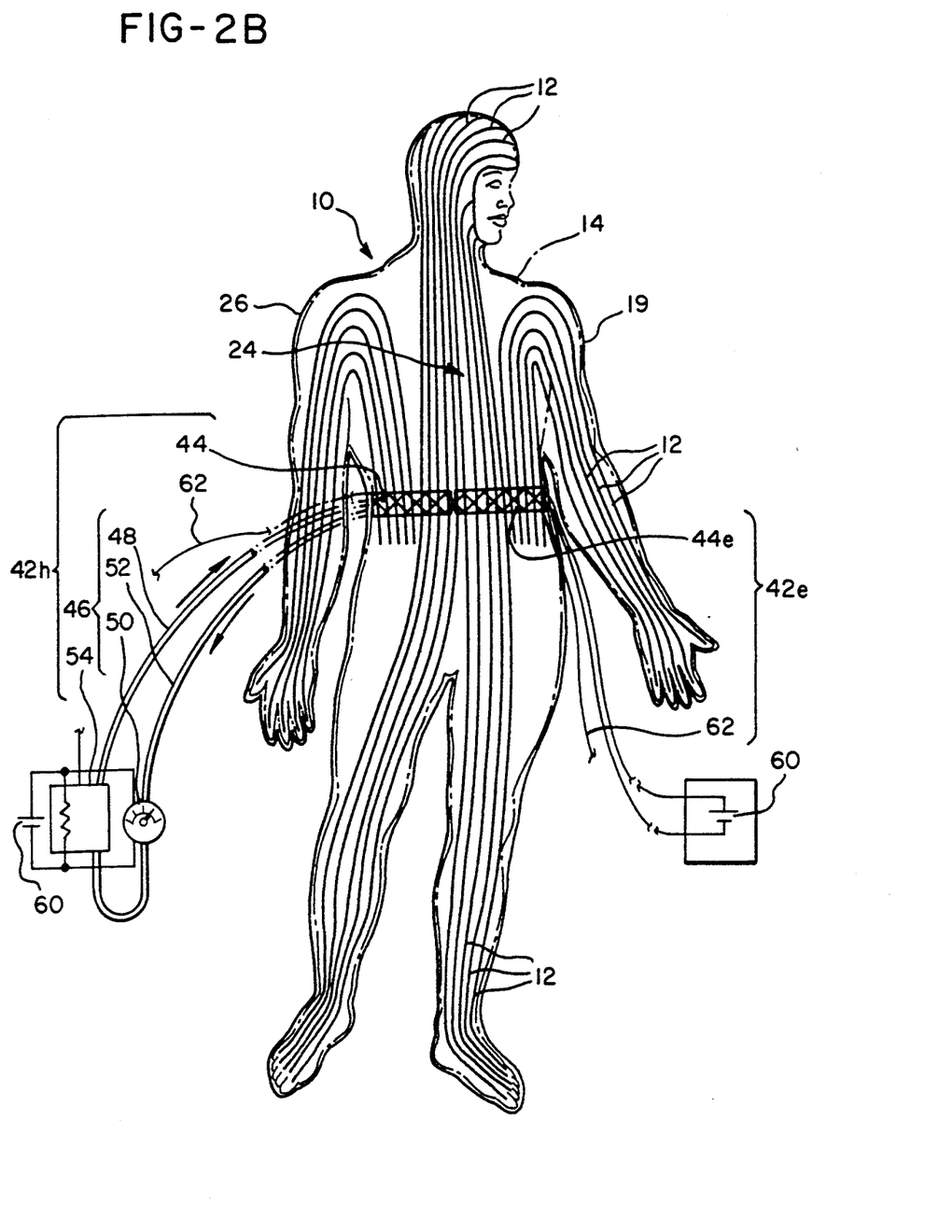

Referring now to FIGS. 2A and 2B, in a second embodiment, the garment 10 of the first embodiment further includes a heat exchanger, 42c and 42h, respectively. A portion of each heat exchanger 42c, 42h intersects one or more of the heat pipes 12 to provide heat transfer between one or more portions of the body 14 and the heat exchanger 42c, 42h. The heat exchanger 42c, 42h includes a heat exchanger element 44, preferably disposed in the torso area 24 of the garment 10, a circulating fluid loop 46, and either means for heating 54 in heat exchanger 42h or means for cooling 56 in heat exchanger 42c. Circulating fluid loop 46 consists of tubing 48, a pump 50, and circulating heat transfer fluid 52. Referring to FIG. 2B, where the garment 10 is to be used in cold environments, the heat exchanger 42h includes means for heating 54 the circulating fluid 52.

Referring to FIG. 2A, where the garment 10 is used in hot environments, the heat exchanger 42c includes means for cooling 56 the circulating fluid 52. By way of example, and not limitation, the means for cooling 56 may be a portable bath cooler which, as a closed system, circulates fluid through a probe for immersion into an open bath. This type of system may also be modified for heating, and thus may also be used as a means for heating 54 in heat exchanger 42h. This type of system may also be modified to cool or heat a manifold containing flexible heat pipes, to cool or heat the human body. Portable bath coolers may be obtained commercially, for example as model no. CC-65A with heat removal at $-50°$ C. of 50 watts, from Neslab Instruments, Inc., Portsmouth, N.H. Other commercially available means for heating 54 and cooling 56, and heat exchanger elements 44 may be used in accordance with the present invention, after modification or special design for use with heat pipes 12. Pump 50, means for heating 54, and means for cooling 56 are connected to a source of electrical power (not shown).

Alternatively, as shown in FIG. 2B, the heat exchanger, denominated 42e includes a heat exchanger element 44e having electrical resistance heaters (not shown). Heat exchanger element 44e is, preferably, disposed in the torso area 24, and connected to a source of electrical power (not shown). By way of example, and not limitation, heat exchanger element 44e may be a thermofoil heater of thin, flexible, etched-foil heating elements laminated between insulating layers of materials such as Kapton ®, Nomex ®, or silicone rubber. Such thermofoil heaters are commercially available from Minco Products, Inc. of Minneapolis, Minn. The flexibility of Kapton insulated heaters allows them to have extremely small bend radii, approximately 0.75 millimeters, which makes them amenable for use on the human body. The heaters can be specified to any size, watt density, and input voltage. The shape may, thus, be specified to accommodate insertion of heat pipes 12. The means for heating 42e may further include means for controlling temperature 62, such as temperature sensors in the heat exchanger 44e which attach to controllers for temperature regulation. Where a portable garment 10 is required, the source of electrical power which is attached to pump 50, means for heating 54, means for cooling 56, or heat exchanger element 44e is, preferably, a rechargeable battery pack 60, as shown in FIG. 2B. The heat exchangers 42h, 42c and 42e each, further, preferably include means for controlling temperature 62, such as described above. Temperature control is of particular interest where the present invention is used for deliberate inducement of hyperthermia for medical treatment, or to provide controlled heating or cooling for hypothermia or hyperthermia patients. Because of the very high thermal conductivity of heat pipes 12, they are nearly isothermal in operation, and their temperature can be controlled with substantial accuracy.

Figure 3A:
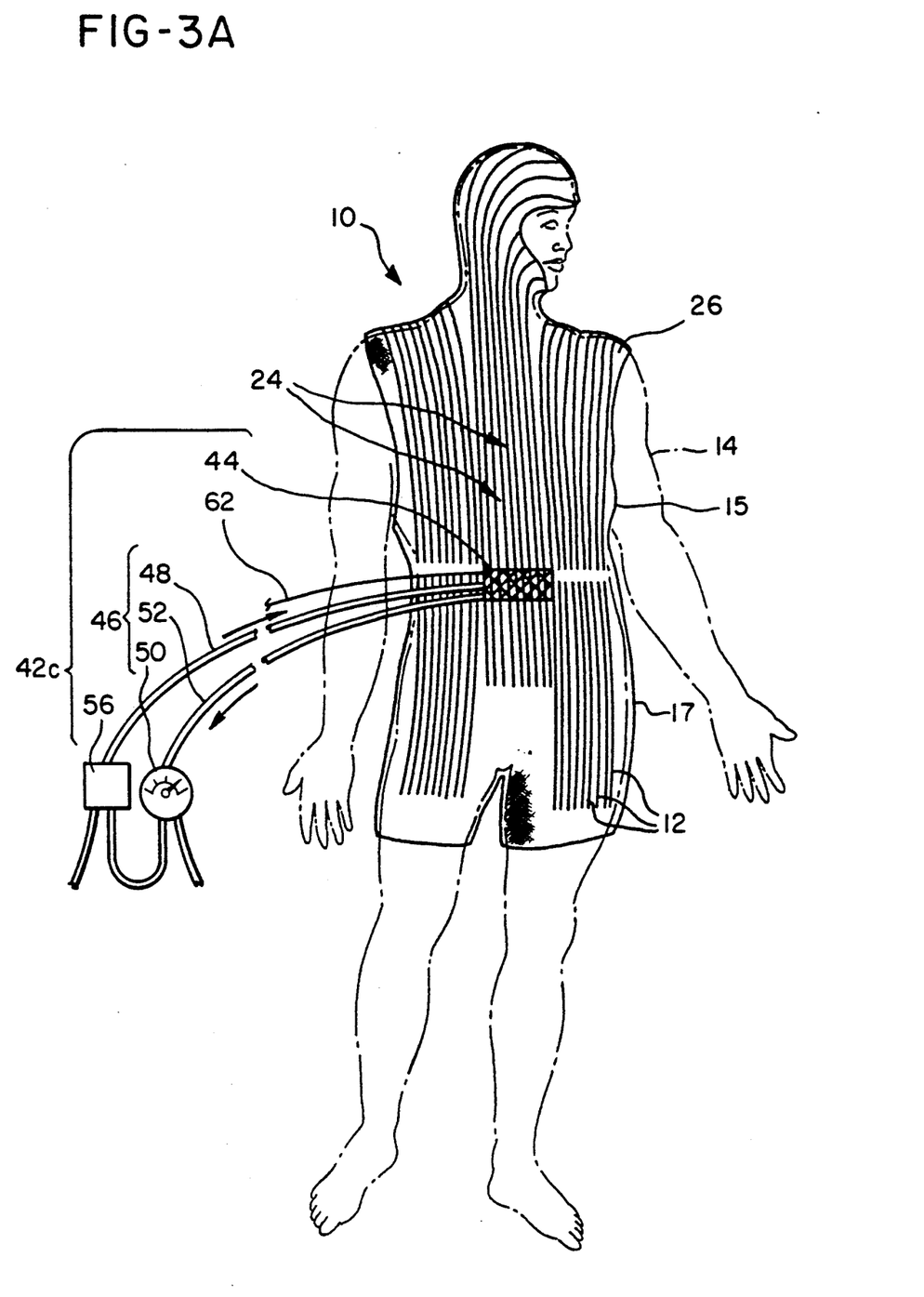
FIGS. 3A and 3B are schematic diagrams of the garment of the present invention in accordance with the third embodiment including means for cooling and means for heating at least some of the heat pipes, respectively.
Figure 3B:
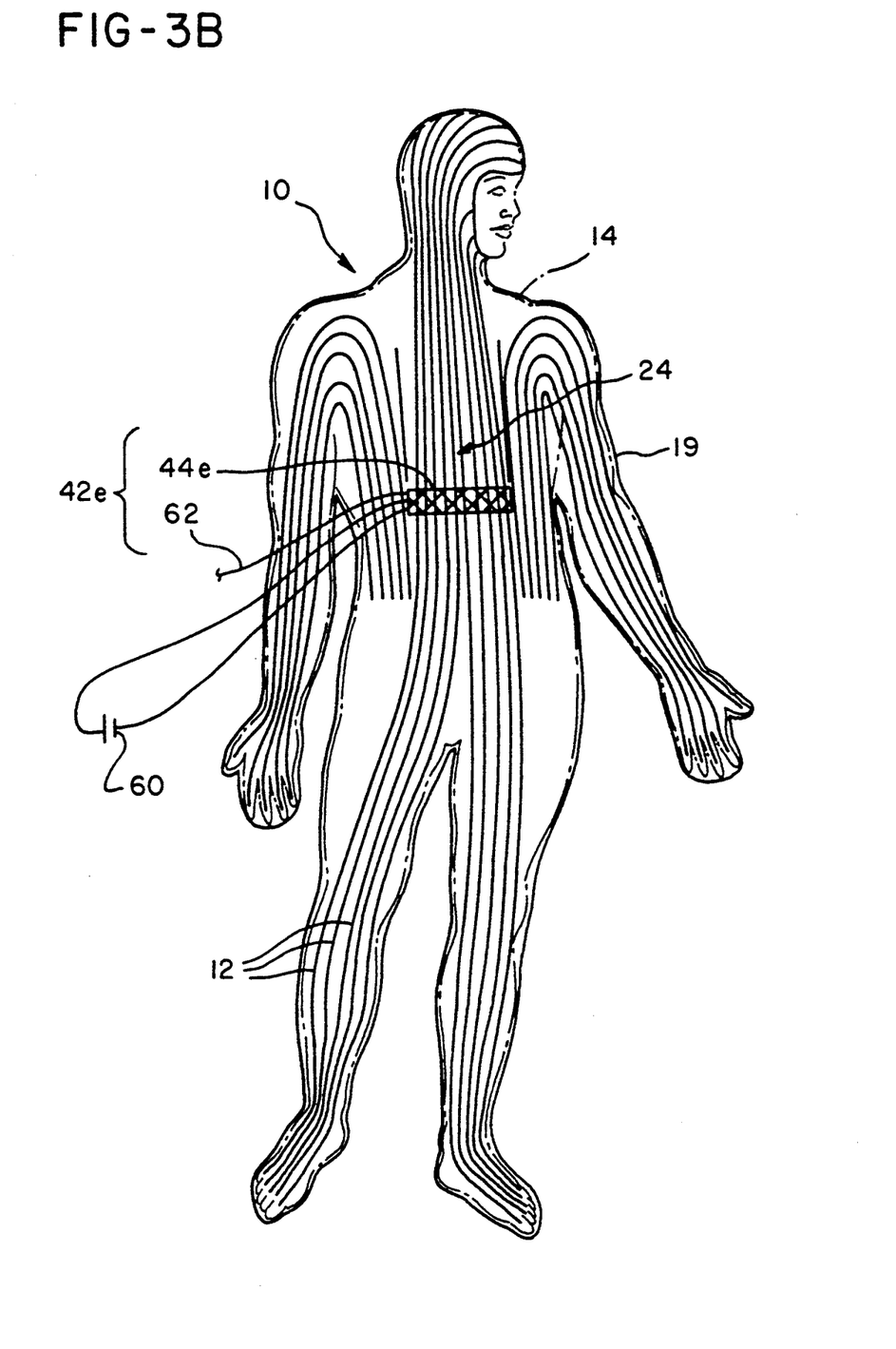

Referring to FIGS. 3A and 3B, a third embodiment of the garment 10 of the present invention includes a heat exchanger 42h, 42e, or 42c of the second embodiment to provide heating or cooling from the heat exchanger 42h, 42e, or 42c to at least one portion of a body 14 by connecting heat exchanger 44 or 44e to one or more heat pipes 12, while maintaining one or more heat pipes 12 to provide heat transfer between portions of a body 14 in accordance with the first embodiment. As shown, for example, in FIG. 3A, cooling is provided to the head and abdomen by heat exchanger 42c, while heat is transferred from the abdomen to the thighs and upper torso areas for dissipation. As shown, for example, in FIG. 3B, heat is provided to the head, legs and feet by heat exchanger 42h, while heat is transferred from one area of the torso 24 to other parts of the torso 24, arms, and hands to warm the individual's extremities.

Figure 4:
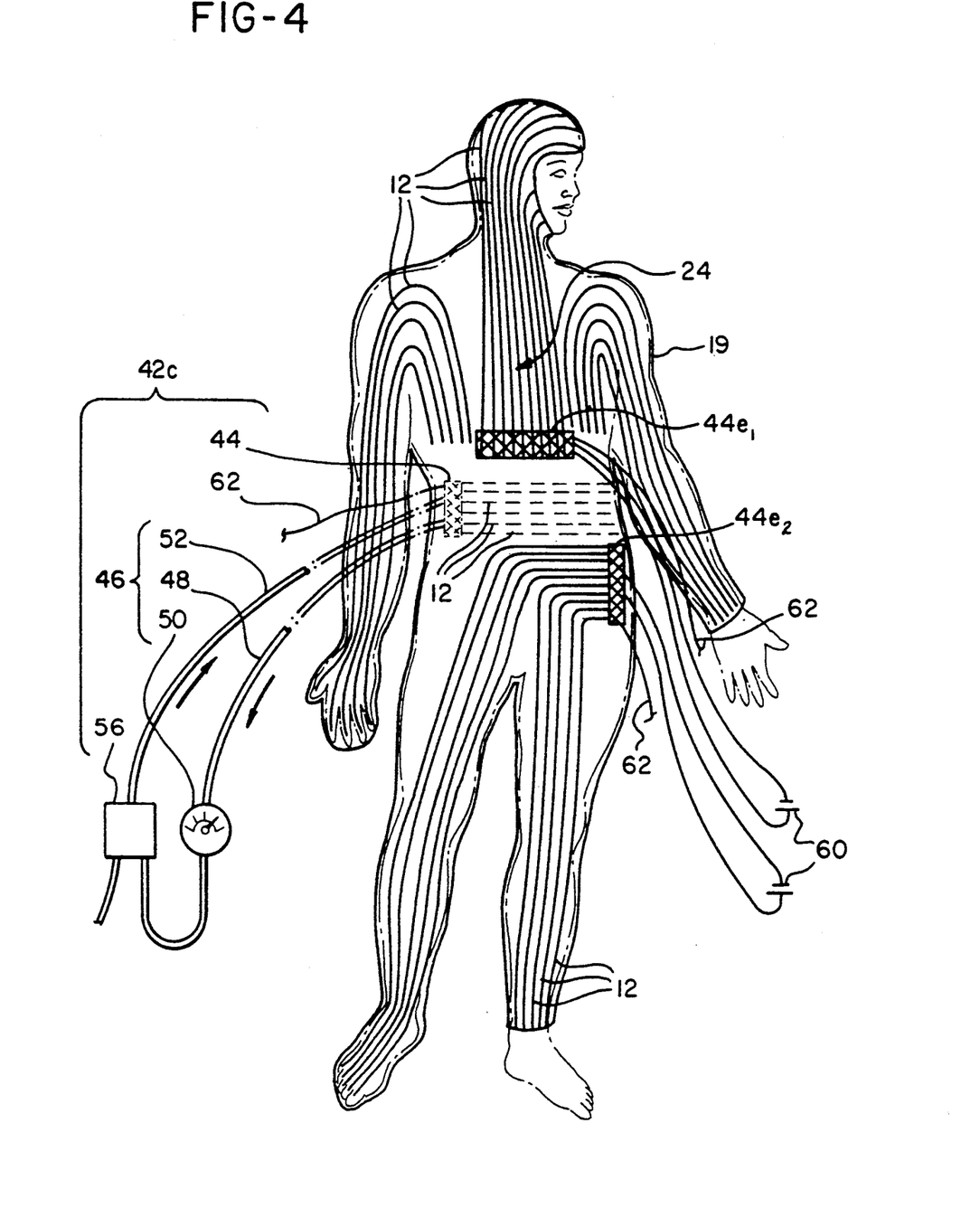
FIG. 4 is a schematic diagram of the garment of the present invention in accordance with the fourth embodiment including two heat exchangers.

Referring now to FIG. 4, in a fourth embodiment, the garment 10 of the present invention includes at least two heat exchangers 42c, 42e, or 42h (not shown) which intersect separate groups of one or more heat pipes 12 to provide heat transfer between separate portions of a body 14 and the heat exchangers 42c and 42e, or 42h (not shown), permitting selective and simultaneous heating or cooling of separate portions of the body 14. For example, in a garment 10, such as the body suit shown, this fourth embodiment provides a means to overcome problems with damage to heat-sensitive organs when whole body hyperthermia is induced for medical treatment. Heat may be applied to major portions of the body 14 to induce hyperthermia with one heat exchanger 42e or 42h (not shown), having heat exchanger element 44e or heat exchanger element 44 (not shown) with means for heating 54 (not shown), while portions of the body 14 having heat-sensitive organs may be cooled with another heat exchanger 42c having means for cooling 56. In FIG. 4, two heat exchanger elements 44e₁, 44e₂ are shown to provide heat to the upper body and legs, respectively, while another heat exchanger 42c cools the abdominal area.

Blankets

Referring now to FIGS. 5A–7, where like numbers represent like elements, a blanket 70 is further provided in accordance with the present invention which regulates body temperature by using a plurality of flexible heat pipes 12 to redistribute body heat and to provide supplemental heat from external sources.

Figure 5A:
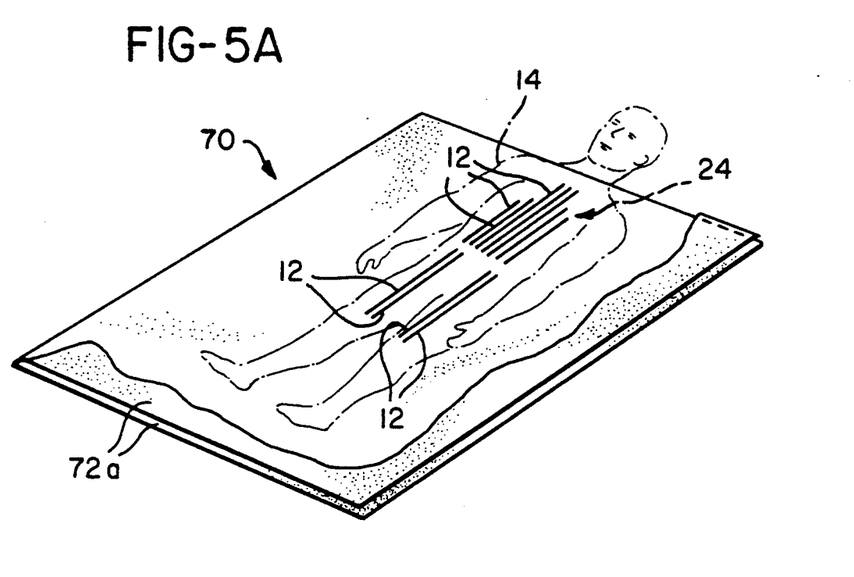
FIGS. 5A and 5B are schematic perspective views of the blanket of the present invention in accordance with the first embodiment.
Figure 5B:
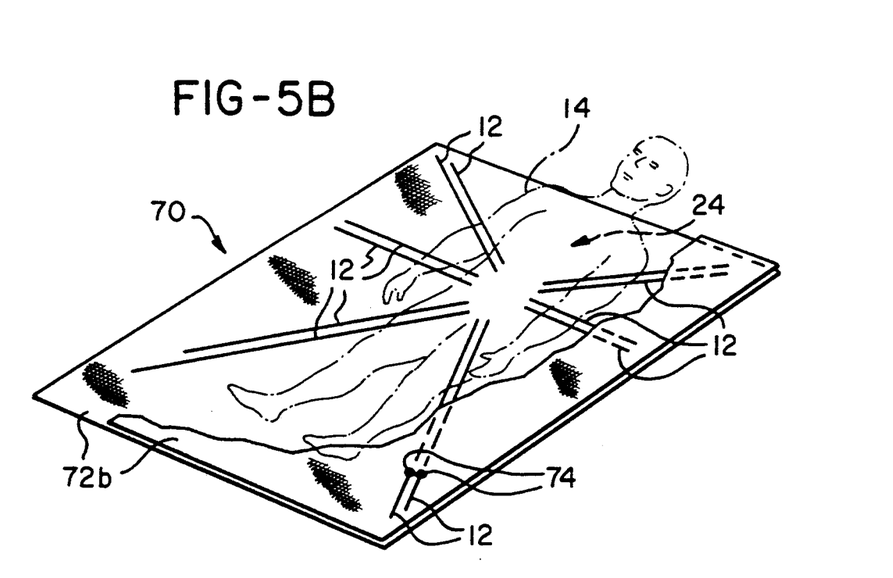

In a first embodiment, shown in FIGS. 5A and 5B, the blanket 70 of the present invention is made of a supporting fabric layer 72a and 72b, respectively, which is sufficiently large to cover at least a part of the torso 24 of a human body 14. A plurality of flexible heat pipes 12 are supported by the fabric layer 72a and 72b. The fabric layer 72a of FIG. 5A is preferably a solid woven fabric to retain heat, while the fabric layer of FIG. 5B is preferably a mesh or net fabric to permit air flow to promote cooling. In accordance with the first embodiment of FIG. 5A, the heat pipes 12 are positioned to provide heat transfer between two or more areas of the blanket 70 and adjacent portions of the body 14.

In the configuration of FIG. 5A, the blanket 70 encourages the body temperature to be regulated to a more uniform level by redistributing heat as needed to provide warming. The heat pipes 12 extend from the torso 24 of the body 14, which is typically warmer, towards other parts of the torso 24 or an extremity, such as the feet or head. The torso 24 is, thereby, used as a heat source.

In the configuration of FIG. 5B, the heat pipes 12 extend outward from the torso 24, head or other heat-sensitive portions of the body 14, to cooler areas at the periphery of the blanket 70, or through apertures 74, as representatively shown for two heat pipes 12, to a surface of the blanket, to discharge heat by radiation or ambient air circulation. Where cooling is intended, heat transfer to the heat pipes 12 is enhanced by direct contact with the skin of body 14.

The first embodiment, thus, permits body temperature to be regulated to a more uniform level, or reduced, by redistributing heat needed to provide warming or cooling for an individual. The first embodiment is useful in satisfying medical needs as well as providing increased comfort for individuals who sweat or develop cold feet during rest or sleep.

Figure 6A:
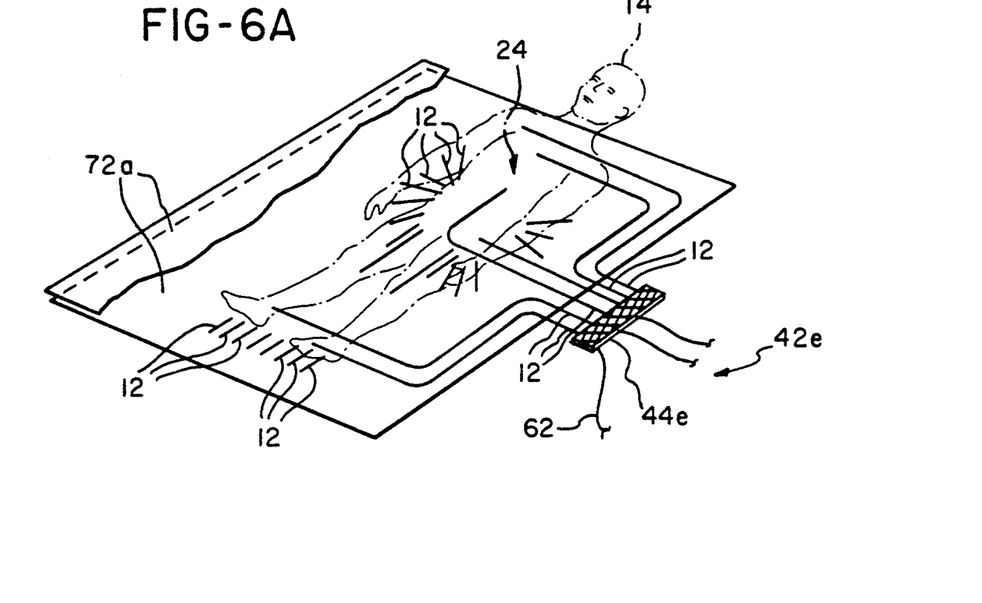
FIGS. 6A and 6B are schematic perspective views of the blanket of the present invention in accordance with the second embodiment including means for cooling and heating, respectively.
Figure 6B:
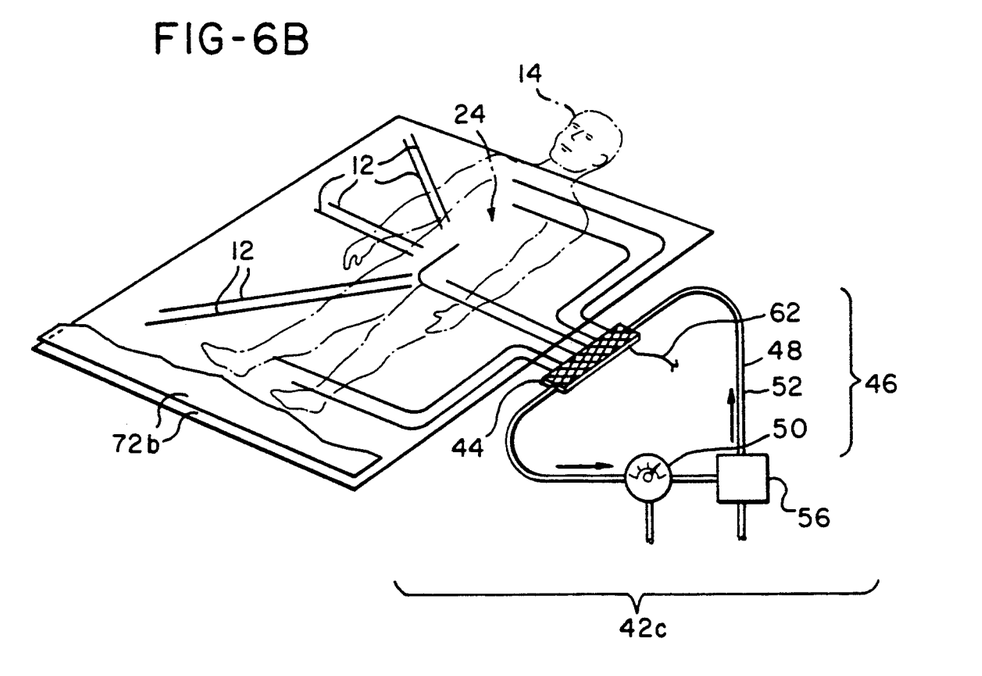

Referring now to FIGS. 6A and 6B, in accordance with a second embodiment, the blanket 70 of the first embodiment further includes one or more heat exchangers 42c, 42e, or 42h (not shown), portions of which intersect one or more of the heat pipes 12. The heat exchangers 42e or 42h (not shown), and 42c, provide heating or cooling, respectively, to at least one area of the blanket 70 and adjacent portions of a body 14 while, simultaneously, one or more heat pipes 12 provide heat transfer between areas of the blanket 70 and adjacent portions of a body 14 in accordance with the structure disclosed in the first embodiment. As in the garment 10, the heat exchangers 42e and 42h, and 42c include an external source of heating or cooling, respectively which enhances heat transfer through the heat pipes 12 to related areas of the blanket 70. Portions of the body 14 adjacent to those areas of the blanket 70, such as the torso 24 or any of the extremities, are, consequently, heated or cooled. As previously discussed with regard to the garment 10, the heat exchangers 42c, 42h (not shown), and 42e include a heat exchanger element 44, 44, and 44e preferably generally centrally disposed in the blanket 70, and a circulating fluid loop 46. Where the heat exchanger 42h is to be used for heating an area of the blanket 70 and adjacent portions of the user, the heat exchanger 42h includes means for heating 54 the circulating fluid 52, and where used to cool, the heat exchanger 42c includes means for cooling 56 the circulating fluid 52. Alternatively, a heat exchanger 42e which may be used for heating, includes a heat exchanger element 44e including electrical resistance heaters (not shown), preferably disposed in the torso 24 area, and an external source of electrical power. Inclusion of a temperature control device, means for controlling temperature 62, is also preferred for reasons discussed above. The second embodiment makes possible the use of the blanket 70 for inducing heating or cooling in one area and adjacent portions of a body 14, while thermal energy is redistributed to or from other areas and portions.

Figure 7:
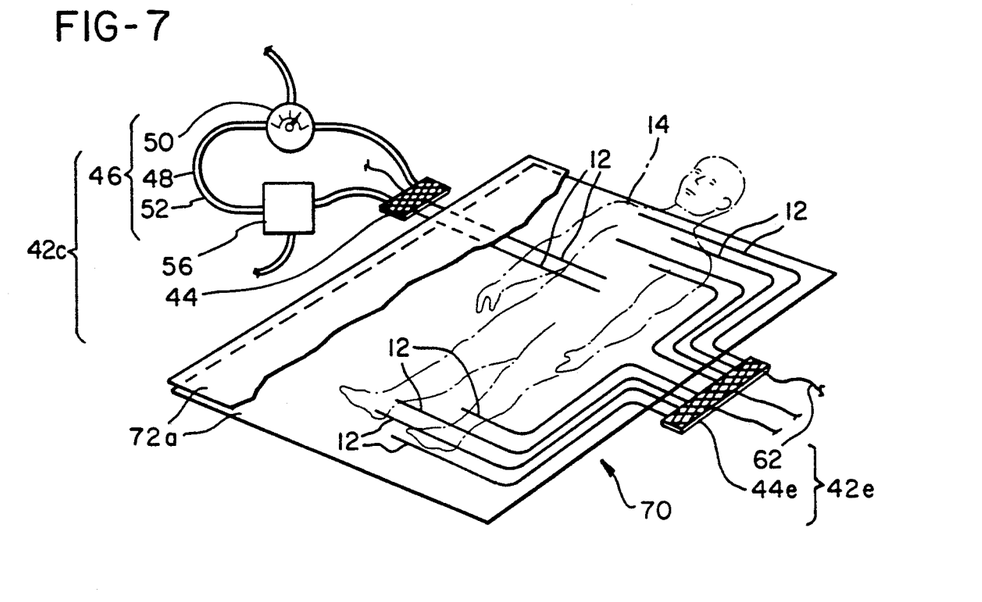
FIG. 7 is a schematic perspective view of the blanket of the present invention in accordance with the third embodiment including both means for cooling and heating.

Referring to FIG. 7, a third embodiment of the blanket 70 of the present invention includes two heat exchangers 42e, 42c, as described in the second embodiment of the blanket, to provide heating and/or cooling from the heat exchangers 44e, 44, respectively, to separate portions of a body 14. Heat exchanger 42c and 42e are shown, however, two heat exchangers $42c_1$, $42c_2$ or $42h_1$, $42h_2$ or $42e_1$, $42e_2$ or other combinations thereof, could be provided. The blanket 70 may be used in the inducement of hyperthermia for medical treatment, while providing cooling to heat-sensitive organs, or may be used in other applications where separate zones are cooled or heated to different temperatures.

Pads

Figure 8:
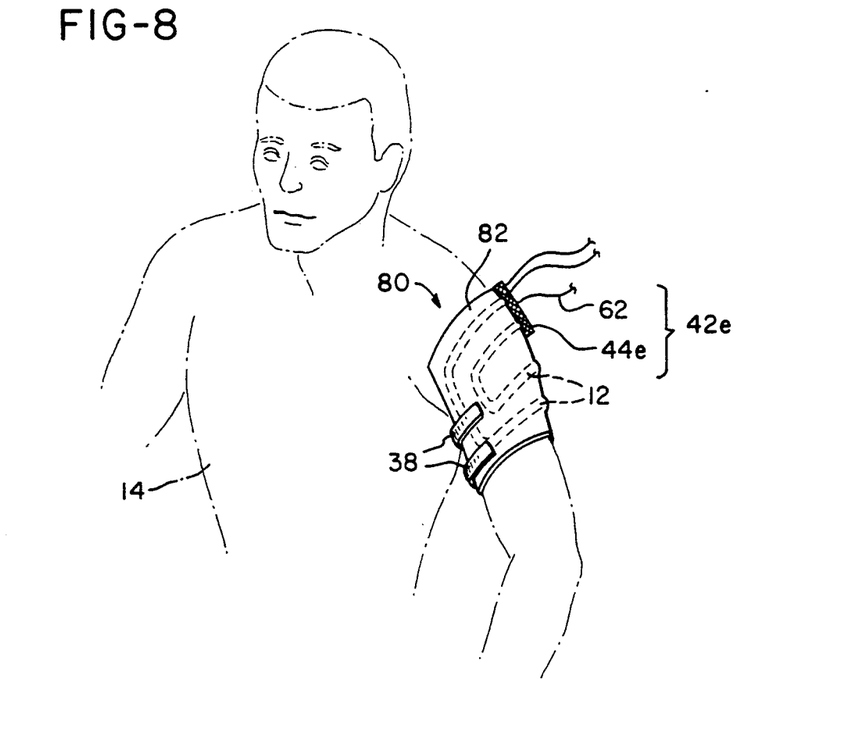
FIG. 8 is a schematic perspective view of the pad of the present invention.

Referring to FIG. 8, the pad 80 of the present invention is shown. Pad 80 is made of one or more a supporting fabric layers 82, which are sufficiently large to cover only a small portion of a body 14. One or more flexible heat pipes 12 are disposed thereon. The pad 80, further, preferably includes a heat exchanger 42e which intersects the heat pipes 12. Alternatively, heat exchanger 42c (not shown) or 42h (not shown) may be used. Regardless, heat exchanger 42e, 42c or 42h may be located entirely remote from the pad 80 or disposed, at least in part, thereon. The heat pipes 12 are supported by the fabric layer 82 and positioned to provide regional or local heat transfer between the heat exchanger 42e and the pad and adjacent portions of the body 14 to which it is attached. Heat pipes 12 may be attached to fabric layers 82 in many ways, either permanently, or by adjustable means for attaching 38, such as velcro connectors. As well, the pad 80 may be attached to itself, as shown by adjustable means for connecting 38, to grip onto the individual when in use.

The pad 80 provides regional or local heat or cooling to the body 14, as needed to provide warming or cooling, primarily for medical applications. However, the pad 80 may also be used to warm portions of individuals who are subject to hypothermia, or cold feet, or to cool areas subject to continued sweating, such as the back or seat of a wheelchair. The heat exchanger 42 used in the pad of the present invention may be any of the fluid or electrical types discussed above with regard to garments 10 and blankets 70.

While certain representative embodiments and details have been shown for purposes of illustrating the invention, it will be apparent to those skilled in the art that various changes in the apparatuses disclosed herein may be made without departing from the scope of the invention, which is defined in the appended claims.

What is claimed is:

1. A garment for body temperature regulation comprising:
   a supporting fabric shaped to cover at least a portion of a body including the torso thereof;
   a plurality of heat pipes supported by said fabric, said plurality of heat pipes positioned to provide heat transfer with one or more portions of said body, and at least one of said plurality of heat pipes removably attached to said fabric by means for connecting, whereby the position of said heat pipe is variable;
   whereby body temperature is influenced at one or more of said one or more portions of said body.

2. The garment of claim 1 wherein said plurality of heat pipes are organized into one or more groups of one or more heat pipes each, and ones of said one or more groups extend between separate portions of said body to exchange heat between said separate portions of said body.

3. The garment of claim 2 wherein at least one of said one or more groups of heat pipes extend between a portion of said torso and at least a portion of an extremity of said body.

4. A garment for body temperature regulation comprising:
   a supporting fabric shaped to cover at least a portion of a body including the torso thereof;
   a plurality of heat pipes supported by said fabric, wherein:
     said plurality of heat pipes are positioned to provide heat transfer with one or more portions of said body; and
     said plurality of heat pipes are organized into one or more groups of one or more heat pipes each, wherein ones of said one or more groups extend between separate portions of said body to exchange heat between said separate portions of said body, and at least one of said one or more groups of heat pipes extend between a portion of said torso and at least a portion of the head of said body;
   whereby body temperature is influenced at one or more of said one or more portions of said body.

5. The garment of claim 3 wherein said extremity comprises an arm of said body.

6. The garment of claim 5 wherein said portion of said arm to which said heat pipes extend comprises the hand.

7. The garment of claim 3 wherein said extremity comprises a leg of said body.

8. The garment of claim 7 wherein said portion of said leg to which said heat pipes extend comprises the thigh.

9. The garment of claim 2 wherein at least one of said one or more groups of heat pipes extend between separate portions of said torso.

10. The garment of claim 1 further comprising a heat exchanger intersecting one or more of said plurality of heat pipes to provide heat transfer between one or more portions of said body and said heat exchanger.

11. The garment of claim 10 wherein at least a part of said heat exchanger is disposed on said torso.

12. The garment of claim 10 wherein said one or more portions of said body include at least a portion of the torso of said body.

13. The garment of claim 10 wherein said one or more portions of said body include at least a portion of an extremity of said body.

14. The garment of claim 10 wherein said heat exchanger includes:
    a heat exchanger element intersecting one or more of said plurality of heat pipes;
    a circulating fluid loop connected to said heat exchanger element; and
    means for cooling fluid circulating in said fluid loop;
    whereby said garment may be used to cool and regulate the body temperature of the wearer.

15. The garment of claim 10 wherein said heat exchanger includes:

a heat exchanger element intersecting one or more of said plurality of heat pipes;

a circulating fluid loop connected to said heat exchanger element; and means for heating fluid circulating in said fluid loop;

whereby said garment may be used to heat and regulate the body temperature of the wearer.

16. The garment of claim 10 wherein said heat exchanger includes:

a heat exchanger element including electric resistance heating elements and intersecting one or more of said plurality of heat pipes; and a source of electrical power;

whereby said garment may be used to heat and regulate the body temperature of the wearer.

17. The garment of claim 10:

wherein said garment comprises at least two heat exchangers, each of said heat exchangers intersecting separate groups of one or more said of heat pipes to provide heat transfer between separate portions of said body and said heat exchangers, respectively;

whereby said garment may selectively and simultaneously heat or cool separate portions of said body.

18. The garment of claim 10 wherein:

said plurality of heat pipes are organized into one or more groups of one or more heat pipes each;

at least one of said one or more groups extend between separate portions of said body to exchange heat between said separate portions of said body; and said plurality of heat pipes intersecting said heat exchanger comprise one or more of said groups and provide heat transfer between portions of said body and said heat exchanger.

19. The garment of claim 1 wherein at least one of said plurality of heat pipes includes:

a flexible tube section;

a wick material substantially comprised of carbon fibers; and a working fluid.

20. The garment of claim 1 wherein said fabric is positioned to separate said plurality of heat pipes from said body.

21. The garment of claim 1 wherein at least one of said heat pipes is positioned to separate said fabric from said body.

22. The garment of claim 4 wherein at least one of said plurality of heat pipes is removably attached to said fabric by means for connecting, whereby the position of said heat pipes is variable.

23. The garment of claim 1 wherein said means for connecting said heat pipes to said fabric comprises velcro means for connecting.

24. The garment of claim 1 wherein said garment substantially comprises a blanket for body temperature regulation wherein:

said supporting fabric comprises a fabric layer sufficiently large to cover at least a portion of the torso of a body;

said plurality of heat pipes are positioned to provide heat transfer between two or more areas of said blanket and portions of a body adjacent to at least one of said areas;

whereby body heat may be redistributed to effect body temperature.

25. The blanket of claim 24 wherein at least one of said plurality of heat pipes extends between a generally central area of said blanket and a generally peripheral area of said blanket, whereby, when said blanket is in use, heat may be transferred between a portion of said torso generally adjacent to said generally central area and an extremity of said body generally adjacent to said peripheral area.

26. The blanket of claim 24 further comprising one or more heat exchangers intersecting one or more of said plurality of heat pipes to further provide heat transfer between areas of said blanket and portions of said body generally adjacent thereto and said one or more heat exchangers.

27. The blanket of claim 26 wherein:

at least one of said one or more heat exchangers cools an area of said blanket; and at least one of said one or more heat exchangers heats a separate area of said blanket;

whereby separate portions of a body generally adjacent to said separate areas of said blanket may be simultaneously heated and cooled.

28. The blanket of claim 24 wherein at least one of said plurality of heat pipes is removably attached to said fabric by means for connecting, whereby the position of said at least one heat pipe is variable.

29. The garment of claim 1 wherein said garment includes at least a pad area for temperature regulation of a body part, wherein:

said supporting fabric is shaped to cover only a portion of a body including the torso thereof;

at least one heat pipe is positioned to provide heat transfer with said portion of said body; and said garment further comprises a heat exchanger intersecting said at least one heat pipe to provide heat exchange with said portion of said body;

whereby the temperature of a body part is regulated.

30. The pad of claim 29 wherein one or more of said at least one heat pipe is removably attached to said fabric by means for connecting, whereby the position of said one or more heat pipes is variable.

31. The garment of claim 4 further comprising a heat exchanger intersecting one or more of said plurality of heat pipes to provide heat transfer between one or more portions of said body and said heat exchanger.

32. A garment for body temperature regulation comprising:

a supporting fabric shaped to cover at least a portion of a body including the torso thereof;

a plurality of heat pipes, at least one of which is adjustably attached to said fabric by means for connecting the heat pipe to the fabric so that the position of the heat pipe is variable, and wherein:

said plurality of heat pipes are positioned to provide heat transfer with one or more portions of said body;

said plurality of heat pipes are organized into one or more groups of one or more heat pipes each, and ones of said one or more groups extend between separate portions of said body to exchange heat between said separate portions of said body; and at least one of said one or more groups of heat pipes extend between a portion of said torso and at least a portion of an extremity of said body;

whereby body temperature is influenced at one or more of said one or more portions of said body.

33. The garment of claim 32 wherein:

said plurality of heat pipes are organized into at least two groups; and each of said at least two groups extends substantially between different, separate portions of said body.

34. The garment of claim 33 wherein portions of said garment are separable from those portions which cover at least a portion of said torso.

35. The garment of claim 33 wherein said garment is separable into a pants section and shirt section.

* * * * *